United States Patent [19]

Ballany et al.

[11] 4,439,439

[45] Mar. 27, 1984

[54] NON-IRRITATING TETRAMISOLE- OR LEVAMISOLE POUR-ON CONPOSITIONS

[75] Inventors: John M. Ballany, Cumbernauld, Scotland; David Henderson, Carlisle, England

[73] Assignee: Janssen Pharmaceutica N.V., Beerse, Belgium

[21] Appl. No.: 356,666

[22] Filed: Mar. 10, 1982

[51] Int. Cl.$^3$ ............................................. A61K 31/425
[52] U.S. Cl. ..................................................... 424/270
[58] Field of Search ......................................... 424/270

[56] References Cited

U.S. PATENT DOCUMENTS

| 3,980,791 | 9/1976 | Shulz et al. | 424/270 |
| 4,018,932 | 4/1977 | Spicer et al. | 424/270 |
| 4,070,476 | 1/1978 | Brooker et al. | 424/270 |
| 4,096,262 | 6/1978 | Andrews et al. | 424/270 |

*Primary Examiner*—Sam Rosen
*Attorney, Agent, or Firm*—Geoffrey G. Dellenbaugh

[57] ABSTRACT

The present invention relates to non-irritating pour-on compositions for combating helmintic infestations in non-human animals, said compositions comprising tetramisole and/or levamisole in a suitable alkoxy-alkanol.

13 Claims, No Drawings

NON-IRRITATING TETRAMISOLE- OR LEVAMISOLE POUR-ON CONPOSITIONS

DESCRIPTION OF THE INVENTION

The method of systemically administering drugs by pouring or spraying a composition, comprising the desired drug, onto any part of the skin is generally known in veterinary medecine as the pour-on method. Drugs, administered following this method, are absorbed by the skin and, after they have penetrated through the skin, they are transmitted systemically within the animal. [see, for example, W. M. Rogoff and P. H. Kohler, J. Econ. Ent., 53, 814–817 (1960) and B. Idson, J. Pharm. Sci., 64, 901–924 (1975)]. In order to facilitate the penetration through the skin the drug is preferably applied in admixture with an appropriate carrier, which may be any liquid, taking up an adequate amount of the anthelminthic and permitting an adequate resorption of the drug through the skin without damaging the tissues. Said carrier may also consist of a mixture of vehicles, the resulting composition being a cream, a suspension or a solution.

In comparison with the parenteral administration methods the pour-on method offers distinct advantages. For example, there is no need to held the animal, sterile precautions are not necessary and especially trained personal is not required.

In comparison with the oral administration methods, the pour-on method has the advantage that each animal receives an exactly defined amount of the desired drug.

Tetramisole, being chemically designated as 2,3,5,6-tetrahydro-6-phenylimidazo[2,1-b]thiazole and the laevo isomer thereof, levamisole, have been described in U.S. Pat. Nos. 3,274,209, respectively 3,463,786. The compounds are powerful anthelmintic agents. Structurally, tetramisole is represented by the formula

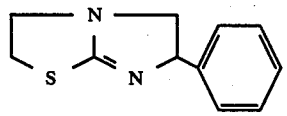
(I)

Anthelmintic pour-on compositions which contain tetramisole, levamisole or an acid-addition salt thereof, have been described in U.S. Pat. Nos. 4,070,476 and 3,980,791. Said compositions have the disadvantage that the carriers, which are the most effective for helping the penetration of the anthelmintic through the skin, are at the same time the most aggressive to the treated skin, resulting in, for example, subcutaneous bleedings, necrosis, hair and skin diseases and, at worst, open wounds. [severe skin irritations, caused by pour-on compositions, are described, e.g., in Veterinär Medizinische Nachrichten 1978 (1), 109–112].

The present invention describes new pour-on compositions for combating helmintic infestations in non-human animals. The compositions of the present invention differ from the prior art compositions by the nature of the solvents in the composition.

This invention relates to pour-on compositions for combating helmintic infestations in non-human animals, which compositions comprise from 4 to 30% by weight of dl- and/or 1-2,3,5,6-tetrahydro-6-phenylimidazo[2,1-b]thiazole in a liquid medium, said medium comprising at least 50% of a solvent consisting of one or more alcohols, having the formula $$HO-(CH_2-CH_2-O)_m-R \qquad (I)$$

wherein m is the integer 1, 2 or 3; and
R is lower alkyl.

As used in the foregoing and in the following definitions all percentages are by weight, and the term "lower alkyl is meant to include straight and branched hydrocarbon radicals having from 1 to 6 carbon atoms such as, for example, methyl, ethyl, 1-methylethyl, 1,1-dimethylethyl, propyl, 2-methylpropyl, butyl, pentyl, hexyl and the like.

Suitable alcohols of formula (I) are, for example, 2-methoxyethanol, 2-(2-ethoxyethoxy)ethanol, 2-(2-butoxyethoxy)ethanol and the like.

The alcohols of formula (I) wherein m is 2 combine a good penetration capacity with a relatively high flashpoint, thus enhancing the safety margin, and therefor these alcohols are especially preferred.

Due to its excellent spreading and run-off properties 2-(2-butoxyethoxy)ethanol is the most preferred alcohol.

Since the anthelmintic activity of tetramisole is exerted essentially by the laevo isomer, in a preferred embodiment levamisole is employed as the anthelmintically active agent.

The amount of the alcohol or alcohols of formula (I) in the medium may vary within rather wide limits, from 50% to 100% by weight of the medium. It has however been found that the incidence of skin irritation shows a tendency to decrease with an increasing content of said alcohol or alcohols. Compositions wherein the medium comprises at least 80% by weight of one or more alcohols of formula (I) are therefor preferred. Particularly preferred are compositions wherein the medium consists essentially of one or more of said alcohols. The most preferred compositions are those wherein the medium consists essentially of 2-(2-butoxyethoxy)ethanol.

Although compositions comprising from 4 to 30% of tetramisole and/or levamisole in one or more alcohols of formula (I) are, as such, very suitable for percutaneous administration, said compositions may possibly contain additives of any nature in minor proportions, which additives do not introduce a significant deleterious effect on the skin. Said additives may facilitate the administration to the skin of the animals and/or may be helpful for preparing the desired composition. Some examples of additives are cited hereinafter.

Minor amounts of aliphatic hydrocarbon mixtures may reduce the surface tension of the compositions and, as such, said aliphatic hydrocarbon mixtures may prevent an excessive adhesion of the applied compositions to the hair and facilitate their spreading over the skin, resulting in an enhanced resorption of the anthelmintic by the skin.

The presence of minor amounts of one or more dipolar aprotic solvents may enhance the penetration rate of the compositions. Suitable dipolar aprotic solvents are, for example, N,N-dimethylformamide, N,N-dimethylacetamide, dimethyl sulfoxide, N-methyl-2-pyrrolidone and the like.

The compositions may also contain other additives such as, for example, substances the taste of which deters animals from licking the applied compositions off the animals treated, pigments making it possible to recognize the treated animals and the like.

Besides tetramisole and/or levamisole, one or more alcohols of formula (I) and, possibly, suitable additives the compositions of the present invention may also contain other pharmaceutically active compounds such as, for example, other substances with anthelmintic and/or insecticidal properties.

The above described compositions are especially characterized by their efficacy and by the complete absence of any skin irritation.

The efficacy of the concerned anthelmintic pour-on compositions can be demonstrated by the eggs-per-gram count technique carried out on faeces samples taken before and after treatment of cattle.

DESCRIPTION OF THE EGGS-PER-GRAM COUNT TECHNIQUE

Prior to treatment cattle weights are estimated by weight band. The backline is clipped out to a width of approximately 8 cm. to eliminate variation in dermal absorption due to differences in hair length and type. On the day of treatment the animals are treated by applying composition no. 1 or composition no. 2 along the backline so that each animal receives 12.5 mg levamisole per kg body weight. Faeces are examined by routine McMaster technique, described in J. Counc. Sci. Industr. Res. Austr. 12, 50 (1939).

Composition no. 1: 10% levamisole in 2-(2-butoxyethoxy)ethanol.

Composition no. 2: 20% levamisole in 2-(2-butoxyethoxy)ethanol.

Table 1 shows the number of eggs per gram of faeces before treatment with composition no. 1 or 2 and 10 days after treatment with composition no. 1 or 2.

TABLE 1

| Breed | Weight in kg | Composition no. | eggs per gram (faeces) pre-treatment | post-treatment |
|---|---|---|---|---|
| BG | 198 | 1 | 200 | 0 |
| BG | 194 | 1 | 300 | 0 |
| BG | 192 | 1 | 200 | 0 |
| F | 222 | 2 | 300 | 0 |
| SG | 222 | 2 | not available | 0 |
| BG | 210 | 2 | 400 | 0 |
| BG | 178 | 2 | 900 | 0 |
| BG | 182 | 2 | not available | 0 |

BG = Blue Grey;
F = Friesian;
SG = Simental/Galloway

Trial works in breeds with different skin and coat characteristics and in extremes of climate indicate that there are no adverse skin reactions. Histological examination of skin biopsies, taken at 3, 9, 28 and 35 days after treatment of 12.5 mg/kg did not cause any macroscopic changes in bovine skin in comparison with untreated controls.

Consequently, the compositions of the present invention combine good anthelmintic efficacy with excellent skin tolerance, even in warm climates where none of the hitherto used composition has proven completely acceptable.

The hereinabove described compositions can generally be prepared in a conventional manner by stirring intensively the tetramisole and/or levamisole with one or more alcohols of formula (I), optionally comprising one or more suitable additives.

Although the hereinabove described compositions are useful for combating helmintic infestations in all non-human animals, in general they are especially preferred for the treatment of cattle and sheep.

The following examples are intended to illustrate and not to limit the scope of the present invention.

EXAMPLE I 10 grams of levamisole and 60 grams of 2-(2-butoxyethoxy)ethanol are mixed intensively untill all levamisole enters solution and the whole is diluted with 30 g 2-(2-butoxyethoxy)ethanol.

EXAMPLE II

Following the procedure described in Example I the following compositions are also prepared:

Composition 1:
 5 g. levamisole
 5 g. 2-propanol
 2 g. N-methyl-2-pyrrolidone
 88 g. 2-(2-butoxyethoxy)ethanol.

Composition 2:
 20 g. levamisole
 80 g. 2-(2-butoxyethoxy)ethanol.

What is claimed is:

1. A pour-on composition for combating helmintic infestations in non-human animals comprising from 4 to 30% by weight of dl- and/or 1-2,3,5,6-tetrahydro-6-phenylimidazo[2,1-b]thiazole in a liquid medium, said medium comprising at least 50% by weight of one or more alcohols of the formula $$HO-(CH_2-CH_2-O)_m-R \qquad (I)$$

wherein m is the integer 1, 2 or 3; and R is a lower alkyl radical.

2. A pour-on composition according to claim 1 wherein said medium comprises at least 80% by weight of one or more alcohols of the formula (I) as defined in claim 1.

3. A pour-on composition according to claim 1 wherein said medium essentially consists of one or more alcohols of the formula (I) as defined in claim 1.

4. A pour-on composition for combating helmintic infestations in non-human animals comprising from 4 to 30% by weight of dl- and/or 1-2,3,5,6-tetrahydro-6-phenyl-imidazo[2,1-b]thiazole in a liquid medium, said medium comprising at least 50% by weight of one or more alcohols of the formula $$HO-(CH_2-CH_2-O-)_2-R \qquad (I-a)$$

wherein R is a lower alkyl radical.

5. A pour-on composition according to claim 4 wherein said medium comprises at least 80% by weight of one or more alcohols of the formula (I-a) as defined in claim 4.

6. A pour-on composition according to claim 4 wherein said medium essentially consists of one or more alcohols of the formula (I-a) as defined in claim 4.

7. A pour-on composition for combating helmintic infestations in non-human animals comprising from 4 to 30% by weight of dl- and/or 1-2,3,5,6-tetrahydro-6-phenyl-imidazo[2,1-b]thiazole in a liquid medium, said medium comprising at least 50% by weight of 2-(2-butoxyethoxy)ethanol.

8. A pour-on composition according to claim 7 wherein said medium comprises at least 80% by weight of 2-(2-butoxyethoxy)ethanol.

9. A pour-on composition according to claim 7 wherein said medium essentially consists of 2-(2-butoxyethoxy)ethanol.

10. A pour-on composition for combating helmintic infestations in non-human animals which comprises from 4 to 30% by weight of 1-2,3,5,6-tetrahydro-6-phenyl-imidazo[2,1-b]thiazole in a liquid medium, said medium comprising at least 50% by weight of 2-(2-butoxyethoxy)ethanol.

11. A pour-on composition according to claim 10 wherein said medium comprises at least 80% by weight of 2-(2-butoxyethoxy)ethanol.

12. A pour-on composition according to claim 10 wherein said medium essentially consists of 2-(2-butoxyethoxy)ethanol.

13. A method of combating helmintic infestations in non-human animals which comprises topically administering to said animals a composition as claimed in any one of the claims 1 to 12.

* * * * *